United States Patent
Akama et al.

(10) Patent No.: US 9,610,066 B2
(45) Date of Patent: Apr. 4, 2017

(54) METHOD OF COLLECTING CELLS

(71) Applicant: SYSMEX CORPORATION, Kobe-shi, Hyogo (JP)

(72) Inventors: Kenji Akama, Kobe (JP); Nobuyasu Hori, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 118 days.

(21) Appl. No.: 14/722,472

(22) Filed: May 27, 2015

(65) Prior Publication Data
US 2015/0353892 A1 Dec. 10, 2015

(30) Foreign Application Priority Data
Jun. 6, 2014 (JP) .................................. 2014-117701

(51) Int. Cl.
*A61K 35/28* (2015.01)
*A61B 10/02* (2006.01)
*C12N 5/0775* (2010.01)

(52) U.S. Cl.
CPC .......... *A61B 10/025* (2013.01); *C12N 5/0663* (2013.01); *A61B 2010/0258* (2013.01); *A61K 35/28* (2013.01)

(58) Field of Classification Search
None
See application file for complete search history.

(56) References Cited

U.S. PATENT DOCUMENTS

2004/0215102 A1* 10/2004 Ikehara .............. A61B 10/0096
600/562
2012/0064537 A1 3/2012 Ross

OTHER PUBLICATIONS

Communication dated Jun. 10, 2016 from the U.S. Patent and Trademark Office in U.S. Appl. No. 14/673,199.
Uygun B. et al., "Organ reengineering through development of a transplantable recellularized liver graft using decellularized liver matrix," Technical Reports: Nature Medicine, vol. 16 | No. 7 | Jul. 2010, pp. 814-821.
Pereira S. et al., "Gallstone Dissolution with Oral Bile Acid Therapy: Importance of Pretreatment CT Scanning and Reasons for Nonresponse," Digestive Diseases and Sciences, vol. 42, No. 8 (Aug. 1997) pp. 1775-1782.
Satoko Kakiuchi et al., "Flow Cytometric Analyses on Lineage-Specific Cell Surface Antigens of Rat Bone Marrow to Seek Potential Myelotoxic Biomarkers: Status After Repeated Dose of 5-Fluorouracil", The Journal of Toxicological Sciences, 2004, pp. 101-111, vol. 29, No. 2.
Kiyoshi Matsumoto, "Detection of Myelotoxicity in the Safety Study", Shinshu Igaku Zasshi, 1992, pp. 241-252, vol. 40, No. 3.

* cited by examiner

*Primary Examiner* — Soren Harward
*Assistant Examiner* — Paul D. Pyla
(74) *Attorney, Agent, or Firm* — Sughrue Mion, PLLC

(57) ABSTRACT

Disclosed is a method of collecting cells including the steps of: preparing a processed-bone comprising a bone extracted from a living body, a covering agent and first and second holes, wherein an outer surface of the bone is covered with the covering agent attached to the outer surface of the bone, and the first and second holes penetrate through the covering agent and the outer surface of the bone into the interior of the bone; introducing a liquid into the processed-bone from the first hole; and collecting a cell-containing liquid from the second hole.

20 Claims, 3 Drawing Sheets

METHOD OF COLLECTING CELLS

CROSS REFERENCE TO RELATED APPLICATIONS

This application claims priority from prior Japanese Patent Application No. 2014-117701, filed on Jun. 6, 2014, entitled "METHOD OF COLLECTING CELLS AND PROCESSED-BONE USED FOR THE SAME," the entire contents of which are incorporated herein by reference.

TECHNICAL FIELD

The present invention relates to a method of collecting cells using a processed-bone having an outer surface covered with a covering agent.

BACKGROUND

Usually, the surface of a bone is covered with periosteum. The inside of the periosteum consists of bone substance (compact substance and spongy substance). In the bone substance, there is an inner cavity filled with bone marrow, which is called "medullary cavity." Various cells are present in the bone marrow, and these cells are collectively referred to as "bone marrow cells."

The bone marrow is known to be a hematopoietic organ. The bone marrow cells include mature and immature blood cells and hematopoietic stem cells. Thus, the bone marrow is collected from the bones of laboratory animals for the purpose of immunological studies and toxicity tests. In the case of large animals such as dogs and monkeys, the bone marrow can be directly collected from the bone of a subject under anesthesia using a bone marrow needle. On the other hand, in the case of small animals such as rats and mice, the bone marrow can be collected by extracting the femur from a subject, excising both the ends (epiphyses) of bones, injecting a liquid such as fetal bovine serum (FBS) into the bone from the cut surface using a syringe having an injection needle attached thereto so as to wash out the bone marrow (refer to, for example, Kakiuchi S. et. al., J. Toxicol. Sci., vol. 29, No. 2, p.p. 101-111, 2004).

The present inventors have applied the above method of collecting cells in a bone by injecting a liquid into the interior of the bone to bones extracted from large animals. That is, the present inventors have made two holes spaced in a longitudinal direction in the femur extracted from a pig, introduced physiological saline from one of the holes, and tried to collect a cell-containing liquid from the other hole. Surprisingly, the cell-containing liquid has been hardly collected from the hole, and most of the liquid has leaked from the surface of the bone. In this manner, the present inventors have found that, in the method of collecting cells by introducing a liquid into the interior of a bone, the liquid leaks from the surface of the bone, whereby the cells in the bone cannot be collected at a high yield.

SUMMARY OF THE INVENTION

The scope of the present invention is defined solely by the appended claims, and is not affected to any degree by the statements within this summary.

As a result of intensive studies, the present inventors have found that, in the method of collecting cells in a bone by introducing a liquid into the interior of the bone, the leakage of the cell-containing liquid from the outer surface of the bone can be suppressed by covering the outer surface of the bone with a covering agent, and completed the present invention.

Therefore, the present invention provides a method of collecting cells including the steps of: preparing a processed-bone comprising a bone extracted from a living body, a covering agent and first and second holes, wherein an outer surface of the bone is covered with the covering agent attached to the outer surface of the bone, and the first and second holes penetrate through the covering agent and the outer surface of the bone into the interior of the bone; introducing a liquid into the processed-bone from the first hole; and collecting a cell-containing liquid from the second hole.

DETAILED DESCRIPTION OF THE PREFERRED EMBODIMENTS

The preferred embodiments of the present invention will be described hereinafter with reference to the drawings.

Figure 1:
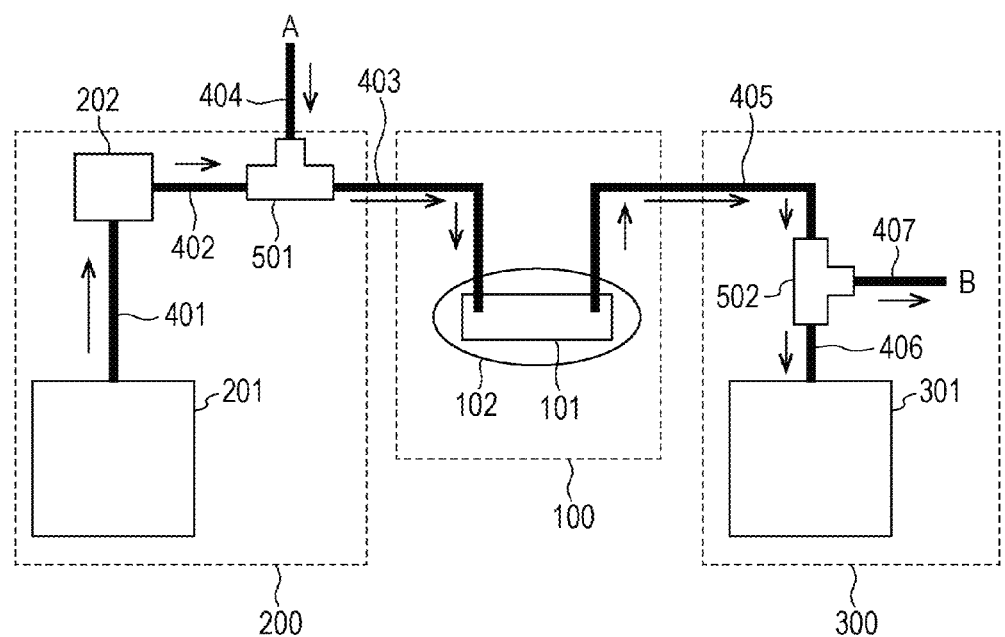
FIG. 1 is a pattern diagram of a perfusion system suitable for the method of collecting cells of the present embodiment.

The method of collecting cells of the present embodiment (hereinafter, simply referred to as "method") is a method including introducing a liquid from the first hole of the processed-bone, and collecting a cell-containing liquid from the second hole. The method of the present embodiment may be carried out manually. The method may also be carried out by a perfusion system using a liquid feeding pump. An example of the perfusion system suitable for the method of the present embodiment is shown in FIG. 1. The perfusion system shown in FIG. 1 mainly includes a bone 101 (processed-bone) covered with a covering agent 102, a perfusate bottle 201, a liquid feeding pump 202, a collecting bottle 301, tubes 401 to 407 which connect respective components, and three-way cocks 501 and 502. In FIG. 1, each of the arrows indicates a direction of the flow of the liquid as a perfusate.

In the perfusion system shown in FIG. 1, an arbitrary component can be added to the liquid through the tube 404 from a feeding port A. For example, cells are added into the liquid and the cell-containing liquid is introduced into the interior of the bone so that changes in the cells collected can be observed. Therefore, the cells to be collected by the method of the present embodiment include not only bone marrow cells but also cells externally added. It is possible to take a sample of the liquid which contains the cells collected in the collecting bottle 301 from a collecting port B. Hereinafter, the steps of the method of the present embodiment will be described.

In the method of the present embodiment, the following step is first performed: the step of preparing a processed-bone comprising a bone extracted from a living body, a covering agent and first and second holes, wherein an outer surface of the bone is covered with the covering agent attached to the outer surface of the bone, and the first and second holes penetrate through the covering agent and the outer surface of the bone into the interior of the bone.

The bone to be used for preparing a processed-bone may be a bone of any animal such as fish, amphibians, reptiles, birds, and mammals. Among them, bones of mammals except humans are particularly preferred. As such mammals, animals to be used for animal experiments or livestock are preferred. Examples thereof include pigs, cattle, horses, goats, sheep, monkeys, dogs, cats, rabbits, guinea pigs, rats, and mice.

The kind of bone is not particularly limited. It may be any of long, short, flat and irregular bones as long as it is a hard bone. Examples of the long bones include humerus, radius, ulna, metacarpal, femur, tibia, fibula, and metatarsal. Examples of the short bones include carpus and tarsal. Examples of the flat bones include parietal bone, sternum, rib, and ilium. Examples of the irregular bones include vertebra and scapula.

In the method of the present embodiment, the bone to be used for preparing a processed-bone is preferably a bone immediately after extraction from an animal. In the case where the method of the present embodiment is not performed immediately after extraction of the bone, the extracted bone may be refrigerated. The refrigeration temperature may be a common temperature, for example, 4° C. In the case where the bone is refrigerated immediately after extraction, it is preferable to use the bone within one day after extraction. As for the method of extracting a bone from an animal, the method itself is publicly-known in the art.

The step of preparing a processed-bone may include the steps of covering a bone with a covering agent, and making first and second holes in the bone. In the present embodiment, the order of performing the step of covering a bone and the step of making first and second holes in the bone is not particularly limited. For example, it is possible to cover a bone with a covering agent, and then make holes that penetrate through the covering agent and the outer surface of the bone into the interior of the bone. Alternatively, it is also possible to make, in the bone, holes that penetrate into the interior of the bone, and then cover the bone with the covering agent without filling the holes. In the case where holes are first made in the bone, tubes or rods having the same diameter as that of the holes (preferably injection needles) are inserted into respective holes before the bone is covered with the covering agent, whereby the holes can be kept without being filled with the covering agent.

The first and second holes of the processed-bone are holes that penetrate through the covering agent and the outer surface of the bone into the interior of the bone. In the present embodiment, the position of the holes in the bone is not particularly limited. For example, in the case where holes are made in a portion covered with periosteum such as diaphysis of a long bone, the first and second holes are holes that penetrate through the covering agent and the periosteum as the outer surface of the bone into the interior of the bone. On the other hand, there is no periosteum on the articular surface of the bone, and the articular surface is covered with articular cartilage. Therefore, in the case where holes are made in the articular surface of the bone, the first and second holes are holes that penetrate through the covering agent and the articular cartilage as the outer surface of the bone into the interior of the bone. The means for making holes in the bone is not particularly limited, and a tool such as a needle or a drill may be used.

In the present embodiment, the depth of the first hole is preferably a depth that allows the liquid described later to be introduced from the hole to be in contact with the bone marrow. The depth of the second hole is preferably a depth that allows the cell-containing liquid described later to be collected from the hole. Each of the depths of the first and second holes is, for example, a depth that reaches the bone substance, preferably a depth that reaches the spongy substance, and more preferably a depth that reaches the medullary cavity.

The size of the first and second holes is not particularly limited as long as it is capable of allowing the liquid to be introduced and collecting the cell-containing liquid. For example, the first and second holes may have the same diameter as that of a tube or injection needle which is used to introduce the liquid and collect the cell-containing liquid. The diameter may be appropriately set in a range of from 0.3 mm to 2.1 mm both inclusive.

In the method of the present embodiment, since cells are collected by introducing the liquid into the interior of the bone, it is preferable that there is a certain distance between the first and second holes. The distance between the first hole and the second hole may be appropriately determined according to the size of bone. For example, in the case of a long bone such as femur, the first hole may be made in the diaphyseal portion near one bone end and the second hole may be made in the diaphyseal portion near the other bone end.

In the present embodiment, the first and second holes may each be singular or plural. The number of the first hole may be the same as the number of the second hole or they may differ from each other.

The covering agent is attached firmly to the outer surface of the bone in order to suppress the leakage of the liquid and cells, which are to be collected from the second hole, from the outer surface of the bone. Accordingly, the covering agent is not particularly limited as long as it is a substance, material or product having two properties as follows: it can be attached firmly to the outer surface of the bone; and it can suppress the leakage of the liquid and cells from the outer surface of the bone. Examples of the covering agent include resins, adhesives, polymer membranes, gels, and gypsum, which are publicly-known in the art. One kind or two or more kinds of these covering agents may be used.

In the present embodiment, since cells in the bone are collected together with the liquid described later, the covering agent is preferably water-impermeable. When the bone is dried, the cells in the bone may be damaged. Thus, it is preferable that the covering agent can be attached firmly to the bone, even if the outer surface of the bone is in a moist state.

In the present embodiment, the principle (or form) of firm attachment of the covering agent to the outer surface of the bone is not particularly limited, as long as the covering agent is in contact with the outer surface of the bone with no space therebetween. In other words, the covering agent and the outer surface of the bone may be merely in close contact with each other, may be mechanically bonded to each other, or may physically or chemically interact with each other. As the mechanical bond, there is an anchor effect caused by solidification of the covering agent flowed in a very small concave portion of the outer surface of the bone. As the physical interaction, there are a bond due to van der Waals' forces and an electrostatic interaction. As the chemical interaction, there is formation of a covalent bond or an ionic bond. In the case where a piece of flesh is partially attached to the outer surface of the bone, the surface may be covered with the covering agent without completely removing the piece of flesh, so long as the leakage of the liquid from the outer surface of the bone can be suppressed. In the present specification, the phrase (the covering agent) "is attached firmly to the outer surface of the bone" also means the case where the outer surface of the bone to which a piece of flesh is partially attached is covered with the covering agent.

As the resin as the covering agent, a curable resin, a plastic resin or the like may be used. Examples of the curable resin include thermosetting resins and photo-curable resins. Examples of the plastic resin include thermoplastic resins. Examples of the thermosetting resins include epoxy resins, silicone resins, phenol resins, urea resins, melamine resins, unsaturated polyester resins, phenoxy resins, vinylester resins, furan resins, and diallyl phthalate resins.

Examples of the thermoplastic resins include polyvinyl chloride, polyvinylidene chloride, polystyrene, styrene-acrylonitrile copolymer, high-density polyethylene, medium-density polyethylene, low-density polyethylene, ethylene-vinyl acetate copolymer, polypropylene, polymethyl methacrylate, methacryl-styrene copolymer, cellulose acetate, polyethylene terephthalate, and vinylidene fluoride.

Examples of the photo-curable resins include urethane acrylate, epoxy acrylate, polyester acrylate, polybutadiene acrylate, silicon acrylate, amino resin acrylate, alicyclic epoxy resin, glycidyl ether epoxy resin, urethane vinyl ether, and polyester vinyl ether.

Among the thermosetting resins and thermoplastic resins, there are resins having a property of curing at an ordinary temperature. Examples of the ordinary temperature-curable resin include silicone resins, epoxy resins, phenol resins, and polymethyl methacrylate. These resins are particularly suitable for the use of the covering agent of the method of the present embodiment.

The adhesive as the covering agent may be appropriately selected from inorganic adhesives, natural adhesives, and synthetic adhesives. Examples of the inorganic adhesive include sodium silicate, cement, and plaster.

Examples of the natural adhesive include natural rubber adhesives, casein adhesives, water-resistant starch adhesives, glue, and albumin.

Examples of the synthetic adhesive include epoxy resin-based adhesives, acrylic resin-based adhesives, α-olefin resin-based adhesives, polyethylene resin-based adhesives, polyvinyl acetate resin-based adhesives, vinyl chloride resin-based adhesives, ethylene-vinyl acetate resin-based adhesives, cyanoacrylate-based adhesives, aqueous polymer isocyanate-based adhesives, chloroprene rubber-based adhesives, styrene-butadiene rubber-based adhesives, nitrile rubber-based adhesives, polysulfide-based adhesives, butyl rubber-based adhesives, silicone rubber-based adhesives, polystyrene-based adhesives, polyvinyl acetate-based adhesives, modified silicone-based adhesives, polyolefin-based adhesives, polyurethane-based adhesives, polymethacrylate resin-based adhesives, phenol resin-based adhesives, urea resin-based adhesives, melamine resin-based adhesives, resorcinol-based adhesives, polyester-based adhesives, polyimide-based adhesives, nitrocellulose adhesives, methylcellulose, and carboxymethyl cellulose. These synthetic adhesives may be in the form of a liquid or emulsion. A tape obtained by coating an appropriate substrate with an adhesive, such as an acrylic resin-based pressure-sensitive adhesive tape, may be used.

The polymer membrane as the covering agent may be appropriately selected from a biopolymer membrane and a synthetic polymer membrane. Examples of the biopolymer membrane include polysaccharide membranes such as chitosan, alginate, and pectin membranes; and plant-derived cellulose membranes such as regenerated cellulose and cellulose triacetate membranes. Further, a membrane obtained by alternately laminating chitosan and an alginate is suitable as the covering agent. Examples of the synthetic polymer membrane include polyacrylonitrile, polymethyl methacrylate, polysulfone, polyether sulfone, polyvinylidene chloride, polyvinyl chloride, medium-density polyethylene, low-density polyethylene, polypropylene, and ethylene-vinyl alcohol copolymer membranes. The shape of the polymer membrane is not particularly limited, and it may be appropriately selected from a tape shape, a film shape, and a sheet shape according to the shape of the bone.

The gel as the covering agent may be appropriately selected from gels containing water as a solvent. Examples thereof include agar, gelatin, agarose gel, polyacrylamide gel, and polyhydroxyethyl methacrylate gel.

Gypsum as the covering agent contains calcium sulfate as a main ingredient. In the method of the present embodiment, hemihydrate gypsum, dihydrate gypsum, anhydrous gypsum or the like may be used. For example, a plaster cast which includes burnt gypsum powder and cotton cloth may be used as the covering agent.

In the method of the present embodiment, the collection rate of the introduced liquid is preferably 50% or more, and more preferably 80% or more. With such a collection rate, the cells contained in the liquid collected from the second hole can be suitably used for immunological studies and toxicity tests. Accordingly, it is preferable that the covering agent to be used in the present embodiment is capable of suppressing the leakage of the liquid from the outer surface of the bone so as to collect the liquid from the second hole at the collection rate.

The method of allowing the covering agent to be attached firmly to the outer surface of the bone may be appropriately selected according to the kind or form of the covering agent. For example, in the case of using a covering agent which cures from a liquid state to a solid state, the method includes immersing the bone in the covering agent in the form of liquid or coating the outer surface of the bone with the covering agent in the form of liquid so as to cover the whole bone with the covering agent, and directly curing the covering agent. In the case of using a covering agent which cures from a plastic state, such as putty, the method includes covering the whole bone with the covering agent in the plastic state, and directly curing the covering agent. In the case of using a covering agent in the form of a thin film, the method includes adhering the covering agent to the outer surface of the bone or wrapping the bone in the covering agent so as to cover the whole bone.

In the method of the present embodiment, the step of preparing a processed-bone is first performed, and then the step of introducing a liquid into the processed-bone from the first hole is performed. This step intends to bring the introduced liquid into contact with the inner portion of the periosteum or the articular cartilage of the bone. For example, the liquid is brought into contact with bone substance, preferably spongy substance, and more preferably bone marrow. In the present embodiment, the means for introducing the liquid is not particularly limited. The liquid may be introduced manually using a syringe having an injection needle attached thereto. Alternatively, the liquid may be introduced by a perfusion system using a liquid feeding pump.

The flow rate of the liquid is not particularly limited as long as it is a flow rate at which the cell-containing liquid can be collected from the second hole. The flow rate may be a flow rate which is generally set in the perfusion experiment of organs. The flow rate may be appropriately set, for example, in a range of from 0.01 mL/min to 100 mL/min both inclusive, and preferably in a range of from 0.1 mL/min to 20 mL/min both inclusive. The amount of the liquid is not particularly limited, and the amount may be appropriately selected from, for example, a range of from 0.01 mL to 6000 mL both inclusive.

The kind of liquid to be introduced is not particularly limited as long as it is a liquid which does not affect the survival of cells. Examples thereof include liquid media to be usually used for culturing cells, such as Roswell Park Memorial Institute medium (RPMI medium), Minimum Essential Media (MEM), Dulbecco's Modified Eagle Medium (DMEM), and Ham's F-12 medium; physiological saline, phosphate buffered saline (PBS), organ preservation solutions such as UW solution (University of Wisconsin solution) and ET-Kyoto solution; plasma, serum, and mixtures thereof. The temperature of the liquid to be introduced is not particularly limited. For example, the temperature is from 4° C. to 50° C. both inclusive, preferably from 20° C. to 42° C. both inclusive, and more preferably from 35° C. to 38° C. both inclusive.

An arbitrary ingredient such as a drug, a cell, a nucleic acid, a protein or a mixture thereof may be added to the liquid. These ingredients may be added to the liquid in advance or in the middle of the introduction. For example, in the perfusion system shown in FIG. 1, these ingredients may be introduced into the liquid from the feeding port A.

The kind of drug is not particularly limited. Examples thereof include drugs useful in the survival and maintenance of cells and drugs causing changes in the behavior, activity, and properties of cells. Examples of the drugs useful in the survival and maintenance of cells include vitamins, amino acids, antibiotics, and antifungal agents. Examples of the drugs causing changes in the behavior, activity, and properties of cells include drugs which change the epigenetic state of cells (e.g., a demethylating agent and a histone deacetylase enzyme inhibitor); and drugs which are involved in signal transduction of cells (e.g., lithium chloride). The drugs may be reagents for transfection which is intended to introduce the nucleic acid described later into cells.

The kind of nucleic acid is not particularly limited, and it may be DNA, RNA or a hybrid thereof. The nucleic acid may be either a double strand or single strand nucleic acid. The nucleic acid may be modified with any substance known in the art, such as a dye, an enzyme or a radioactive substance. Examples of the nucleic acid include genes of interest, probes targeting the genes, siRNAs, shRNAs, and morpholino oligos.

The kind of protein is not particularly limited. Examples thereof include proteins causing changes in the behavior, activity, and properties of cells. Examples of the proteins include cytokines, chemokines, cell growth factors, antibodies, and mixtures thereof.

The kind of cell is not particularly limited, and it may be any of undifferentiated, precursor, and differentiated cells. The undifferentiated cells are not particularly limited as long as they do not reach the final differentiation stage of the embryological cell lineage in the living body. Examples of the undifferentiated cells include stem cells and precursor cells. Examples of the stem cells include embryonic stem cells (ES cells), cloned ES cells, induced Pluripotent Stem cells (iPS cells), Multilineage-differentiating Stress Enduring cells (MUSE cells), mesenchymal stem cells, neural stem cells, epithelial progenitor cells, hepatic stem cells, germ stem cells, hematopoietic stem cells, and skeletal muscle stem cells.

Examples of precursor cells include platelet precursor cells, liver precursor cells, heart precursor cells, and neuronal precursor cells. Examples of platelet precursor cells include megakaryocyte precursor cells, megakaryoblasts, and promegakaryocytes. Examples of the liver precursor cells include hepatoblasts, hepatic precursor cells, hepatic stellate precursor cells, hepatic stem/precursor cells, vascular endothelium precursor cells from liver, and mesothelial precursor cells from liver. Examples of the heart precursor cells include cardiac muscle precursor cells and vascular endothelium precursor cells from heart. Examples of the neuronal precursor cells include neuron precursor cells, glial precursor cells, and vascular endothelium precursor cells from cerebral nervous system.

The differentiated cells are not particularly limited as long as they have reached the final differentiation stage of the embryological cell lineage in the living body. Examples of the differentiated cells include mature megakaryocytes, osteoblasts, chondrocytes, adipocytes, hepatocytes, hepatic mesothelial cells, biliary epithelial cells, hepatic stellate cells, hepatic sinusoid endothelial cells, Kupffer cells, pit cells, vascular endothelial cells, pancreatic duct epithelial cells, pancreatic duct cells, centroacinous cells, acinar cells, islets of Langerhans, cardiac muscle cells, fibroblasts, smooth muscle cells, type I alveolar epithelial cells, type II alveolar epithelial cells, Clara cells, ciliated epithelial cells, basal cells, goblet cells, neuroendocrine cells, kultschitzky cells, renal tubular epithelial cells, urothelial cells, columnar epithelial cells, glomerular epithelial cells, glomerular endothelial cells, podocytes, mesangium cells, nerve cells, astrocytes, microglia, and oligodendrocytes.

In the method of the present embodiment, the step of collecting a cell-containing liquid from the second hole is performed. In the present embodiment, the means for collecting the liquid is not particularly limited. The cell-containing liquid may be collected manually using a syringe having an injection needle attached thereto. Alternatively, the cell-containing liquid may be collected by the perfusion system shown in FIG. 1.

In the present embodiment, a series of cycles including introducing a certain amount of liquid, and collecting the cell-containing liquid may be repeated. In the case where the perfusion system shown in FIG. 1 is used, once the step of collecting the cell-containing liquid is started after introduction of the liquid, the introduction step and the collection step may be performed simultaneously.

In the present embodiment, the cells contained in the collected liquid are not limited to bone marrow cells. In other words, in the case where the above cells have been added to the liquid to be introduced, the added cells are the subject of collection. In the case where the added cells are undifferentiated cells or precursor cells, cells derived from such cells (for example, cells differentiated by passage through the interior of the processed-bone) are also the subject of collection.

In the present embodiment, it is preferable that the step of preparing a processed-bone, the step of introducing a liquid, and the step of collecting a cell-containing liquid are performed in a temperature range of from 4° C. to 50° C. both inclusive. The temperature range is more preferably from 15° C. to 42° C. both inclusive, and more preferably from 20° C. to 38° C. both inclusive. The temperature range allows the damage of the cells collected to be minimally suppressed. Therefore, it is preferable that the covering agent is attached firmly to the bone in the above temperature range.

In the present embodiment, the time between the start of the introduction of the liquid and the end of the collection of the liquid depends on the flow rate and the amount of the liquid. The time is, for example, from 30 seconds to 3000 minutes both inclusive. Preferably, the time may be appropriately set in a range of from 1 minute to 1500 minutes both inclusive.

The processed-bone to be used for the above method is also included in the scope of the present invention. The processed-bone has an outer surface of the bone that is covered with a covering agent attached firmly to the outer surface of the bone, a first hole for introducing a liquid into the interior of the bone, and a second hole for collecting a cell-containing liquid. The first and second holes penetrate through the covering agent and the outer surface of the bone into the interior of the bone.

Materials of the bone and the covering agent to be used for the processed-bone of the present embodiment, the method of preparing a processed-bone, and the method of using the bone are the same as those described in the method of collecting cells of the present embodiment.

Hereinafter, the present invention will be described in detail with reference to examples, however, the present invention is not limited thereto.

EXAMPLES

Example 1

In this example, a pig femur covered with a covering agent was perfused with physiological saline using the perfusion system shown in FIG. 1. Then, the collection efficiency of the introduced liquid was confirmed.

1. Preparation of Processed-Bone (1-1) Extraction of Femur and Formation of Holes The femur was extracted from a pig anesthetized with Ketalar (LWD breed, weight: about 30 kg). The obtained femur was kept at 4° C. Two holes having a diameter of 1.2 mm were drilled in the femur using an electric drill. Injection needles (18 G×1½", manufactured by TERUMO CORPORATION) were inserted into the holes.

(1-2) Covering of Bone

As the covering agent, a silicone resin (PDMS: Polydimethyl siloxane) was used. SILPOT184 (Dow Corning Toray Co., Ltd.) and CATALYST SILPOT184 (Dow Corning Toray Co., Ltd.) were mixed at a ratio of 10:1, and the resultant mixture was stirred for 5 minutes. After stirring, the obtained mixture (PDMS solution) was put in a vacuum device and a deaeration treatment was performed for 15 minutes. The femur in a state where the injection needles were inserted into two holes was placed in a plastic case. The deaerated PDMS solution (600 mL) was poured into the plastic case. The plastic case was put in an oven and heated at 40° C. for 5 hours. The PDMS cured to form a processed-bone.

2. Collection of Cells (2-1) Construction of Perfusion System

The present inventors constructed the perfusion system shown in FIG. 1 in order to introduce a liquid into the above processed-bone and collect cells. The perfusion culture system includes a perfusion section 100 which includes a processed-bone, a liquid feeding section 200 for introducing a liquid into the perfusion section 100, a collecting section 300 for collecting a perfusion culture medium discharged from the perfusion section 100, tubes 401 to 407 which connect respective components, a three-way cock 501 for externally introducing an arbitrary ingredient, and a three-way cock 502 for taking a sample of the ingredient. Hereinafter, the perfusion section 100, the liquid feeding section 200, and the collecting section 300 will be described.

a) Perfusion Section 100

In FIG. 1, the processed-bone is illustrated as the bone 101 covered with the covering agent 102. Tubes 403 and 405 (safeed extension tubes, manufactured by TERUMO CORPORATION) were connected to two injection needles inserted into holes of the processed-bone. The hole into which the injection needle with the tube 403 connected thereto was inserted was defined as a first hole for introducing a liquid. The hole into which the injection needle with the tube 405 connected thereto was inserted was defined as a second hole for collecting and introducing a cell-containing liquid.

b) Liquid Feeding Section 200

The perfusate bottle 201 (2002-5000SD, 5 L, manufactured by AS ONE Corporation) and the liquid feeding pump 202 (Master Flex Liquid Feeding Pump 07528-10, manufactured by Yamato Scientific Co., Ltd.) were connected through the tube 401 (C-Flex Pump Tube, product number: 6424-25, manufactured by Yamato Scientific Co., Ltd.). The tube 402 (C-Flex Pump Tube, product number: 6424-25, manufactured by Yamato Scientific Co., Ltd.) was connected to the liquid feeding pump 202. The tubes 402 and 403 were connected to the three-way cock 501 (R-type, Cock-specification 360°, TS-TR2K, manufactured by TERUMO CORPORATION). The tube 404 (C-Flex Pump Tube, product number: 6424-25, manufactured by Yamato Scientific Co., Ltd.) was connected to the three-way cock 501. In this example, the liquid included in the perfusate bottle 201 (physiological saline) was introduced into the interior of the bone from the first hole of the processed-bone by the liquid feeding pump 202.

c) Collecting Section 300

The collecting bottle 301 (2250-0020, manufactured by Thermo Scientific) and the three-way cock 502 (R-type, Cock-specification 360°, TS-TR2K, manufactured by TERUMO CORPORATION) were connected through the tube 406 (C-Flex Pump Tube, product number: 6424-25, manufactured by Yamato Scientific Co., Ltd). The tube 405 was connected to the three-way cock 502, and further the tube 407 (C-Flex Pump Tube, product number: 6424-25, manufactured by Yamato Scientific Co., Ltd.) was connected thereto.

(2-2) Perfusion

Figure 2:
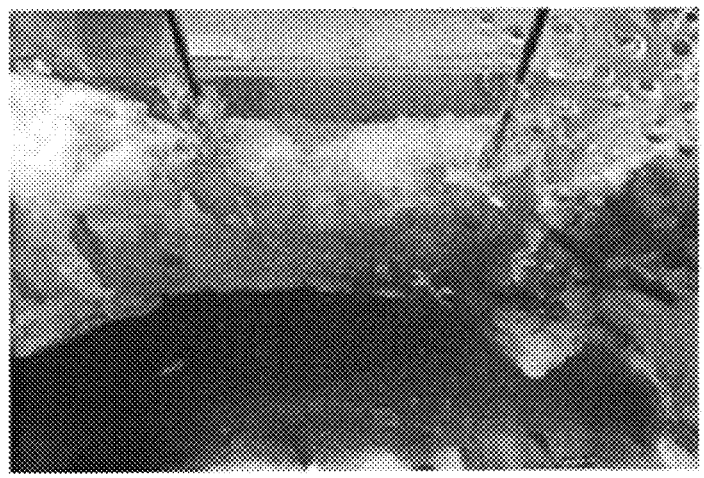
FIG. 2 is a photograph when physiological saline was introduced into the processed-bone covered with polydimethyl siloxane (PDMS) in Example 1.

Physiological saline (100 mL) was introduced into the interior of the bone from the first hole of the processed-bone at a flow rate of 10 mL/min. FIG. 2 shows a photograph when physiological saline was introduced. The introduced physiological saline flowed through the bone marrow, and then the cell-containing liquid was collected from the second hole. The amount of the collected liquid was 99 mL, and the collection rate (the amount of the collected liquid/the amount of the introduced liquid) was 99%.

3. Consideration

Almost all the introduced liquid was collected from the second hole. This shows that there was little leakage of the liquid from the surface of the bone. Consequently, it is thought that the leakage of the liquid from the surface of the bone is suppressed by covering the bone with PDMS, whereby the cells can be collected using the perfusion system.

Comparative Example 1

In this comparative example, the same perfusion experiment as in Example 1 was performed without covering the pig femur with the covering agent.

1. Extraction of Femur and Formation of Holes

Two holes having a diameter of 1.2 mm were drilled in the femur extracted from a pig (LWD breed, weight: about 30 kg), and injection needles (18 G×1½", manufactured by TERUMO CORPORATION) were inserted into the holes, in the same manner as in Example 1. The femur in a state where the injection needles were inserted into the holes was placed on a tray lined with paper towel.

2. Collection of Cells (2-1) Construction of Perfusion System

Tubes were connected to injection needles inserted into holes of the femur, and the same perfusion system as in Example 1 was constructed. The perfusion system was the same as the perfusion system of Example 1 except that the femur of this comparative example was used in place of the processed-bone of the perfusion section 100 of Example 1.

(2-2) Perfusion

Figure 3:
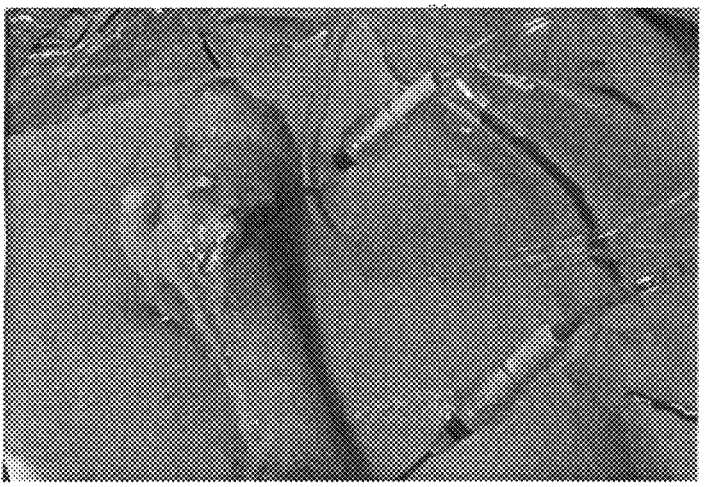
FIG. 3 is a photograph when physiological saline was introduced into an uncovered pig femur in Comparative Example 1.

Physiological saline (100 mL) was introduced into the interior of the bone from the first hole of the processed-bone at a flow rate of 10 mL/min. After introduction of physiological saline, the liquid leaked from various portions on the surface of the femur. FIG. 3 shows a photograph when the leakage of the liquid occurred. As shown in FIG. 3, the leaked liquid was absorbed in the paper towel under the femur. The amount of the liquid collected from the second hole was 9 mL, and the collection rate was 9%.

3. Consideration

It is found that when the bone is perfused with the liquid, the introduced liquid leaks from the surface of the bone. In the perfusion system using the uncovered bone, the collection rate of the introduced liquid is significantly decreased, compared to the result of Example 1. Thus, it is considered to be difficult to collect the cells using the perfusion system.

Example 2

In this example, a bone was covered with the covering agent. Then, holes were drilled in the bone to prepare a processed-bone. It was confirmed whether there was an influence of the order of performing the step of making holes in the bone and the step of covering the bone on the collection efficiency of the liquid. The introduction of the liquid and the collection of cells were performed manually using a syringe, and the collection efficiency of the liquid was confirmed.

1. Preparation of Processed-Bone

The femur was extracted from a pig anesthetized with Ketalar (LWD breed, weight: about 30 kg). The obtained femur was kept at 4° C. A deaerated PDMS solution (600 mL) was prepared using SILPOT184 (Dow Corning Toray Co., Ltd.) and CATALYST SILPOT184 (Dow Corning Toray Co., Ltd.), in the same manner as in Example 1. The femur was placed in a plastic case, and the PDMS solution was poured into the plastic case. The plastic case was allowed to stand at room temperature so as to cure the PDMS. As a result, a processed-bone made of the pig femur covered with PDMS was produced. Two holes having a diameter of 1.2 mm were drilled in the femur covered with PDMS using an electric drill. Injection needles (18 G×1½", manufactured by TERUMO CORPORATION) were inserted into the holes.

2. Collection of Cells

Figure 4:
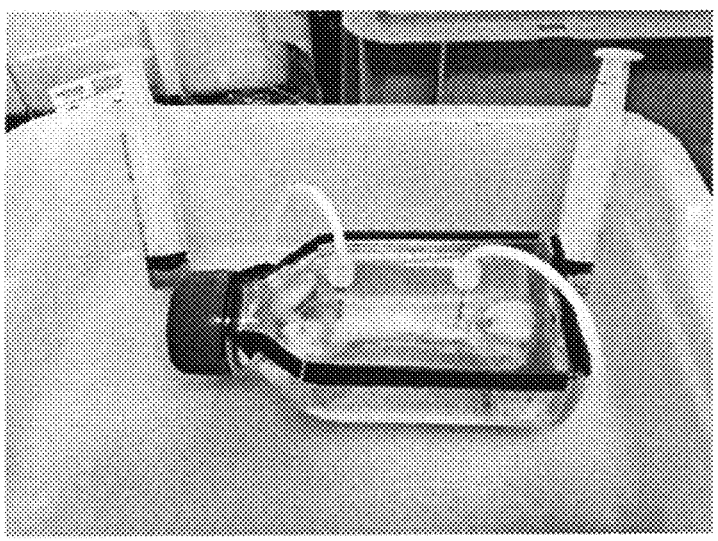
FIG. 4 is a photograph when physiological saline was introduced into the processed-bone covered with PDMS in Example 2.

Tubes (C-Flex Pump Tube, product number: 6424-13, manufactured by Yamato Scientific Co., Ltd.) and syringes (20-mL syringe, manufactured by TERUMO CORPORATION) were connected to two injection needles inserted into the holes of the processed-bone. Physiological saline (25 mL) was introduced into the interior of the bone from one of the syringes. FIG. 4 shows a photograph when physiological saline was introduced. The introduced liquid was collected in the other syringe. Further, the operation of introducing and collecting the liquid was repeated 3 times. Thus, physiological saline (100 mL in total) was introduced into the interior of the bone. The amount of the collected liquid was measured with a measuring cylinder. The amount of the collected liquid was 99 mL, and the collection rate (the amount of the collected liquid/the amount of the introduced liquid) was 99%.

3. Consideration

Almost all the introduced liquid was collected from the second hole. This shows that there is no influence of the order of performing the step of covering the bone and the step of making holes in the bone on the collection efficiency. It is thought that the cells can be collected manually by covering the bone with PDMS.

Comparative Example 2

In this comparative example, an experiment was performed in the same manner as in Example 2 except that the pig femur was not covered with the covering agent.

1. Extraction of Femur and Formation of Holes

Two holes having a diameter of 1.2 mm were drilled in the femur extracted from a pig (LWD breed, weight: about 30 kg), and injection needles (18 G×1½", manufactured by TERUMO CORPORATION) were inserted into the holes, in the same manner as in Example 1. The femur in a state where the injection needles were inserted into the holes was placed on a tray lined with paper towel.

2. Collection of Cells

Figure 5:
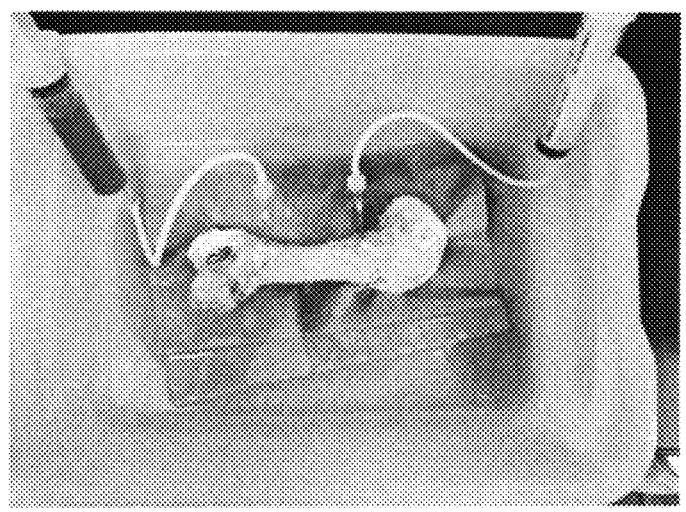
FIG. 5 is a photograph when physiological saline was introduced into an uncovered pig femur in Comparative Example 2.

Tubes (C-Flex Pump Tube, product number: 6424-13, manufactured by Yamato Scientific Co., Ltd.) and syringes (20-mL syringe, manufactured by TERUMO CORPORATION) were connected to two injection needles inserted into the holes of the femur. Physiological saline (25 mL) was introduced into the interior of the bone from one of the syringes. After introduction of physiological saline, the liquid leaked from various portions on the surface of the femur. FIG. 5 shows a photograph when the leakage of the liquid occurred. As shown in FIG. 5, the leaked liquid was accumulated in the tray. The introduced liquid was collected in the other syringe through the second hole. Further, the operation was repeated 3 times. Thus, physiological saline (100 mL in total) was introduced into the interior of the bone. The amount of the collected liquid was 20 mL, and the collection rate (the amount of the collected liquid/the amount of the introduced liquid) was 20%. The amount of the leaked liquid was about 74 mL.

3. Consideration

Similarly to Comparative Example 1, it is found that when the liquid is introduced into the bone, the introduced liquid leaks from the surface of the bone. In the uncovered bone, the collection rate of the introduced liquid is significantly decreased, compared to the result of Example 2. Thus, it is considered to be difficult to collect the cells manually.

Example 3

In this example, the bone was covered with a covering agent different from that of Example 2, and then holes were drilled in the bone to prepare a processed-bone. After that, the kind of covering agent was examined. The introduction of the liquid and the collection of cells were performed manually using a syringe, and the collection efficiency of the liquid was confirmed.

1. Preparation of Processed-Bone (1-1) Extraction of Femur

The femur was extracted from a pig anesthetized with Ketalar (LWD breed, weight: about 30 kg). The obtained femur was kept at 4° C.

(1-2) Covering of Bone

As the covering agent, underwater epoxy putty of an epoxy resin-based adhesive (manufactured by CEMEDINE CO., LTD.) was used. Epoxy putty (60 g) was kneaded and mixed until it became uniformly white. The femur was covered with the mixed epoxy putty. The covered femur was allowed to stand at room temperature so as to cure the epoxy putty. As a result, a processed-bone made of the pig femur covered with epoxy putty was obtained. Two holes having a diameter of 1.2 mm were drilled in the femur covered with epoxy putty using an electric drill. Injection needles (18 G×1½", manufactured by TERUMO CORPORATION) were inserted into the holes.

2. Collection of Cells

Figure 6:
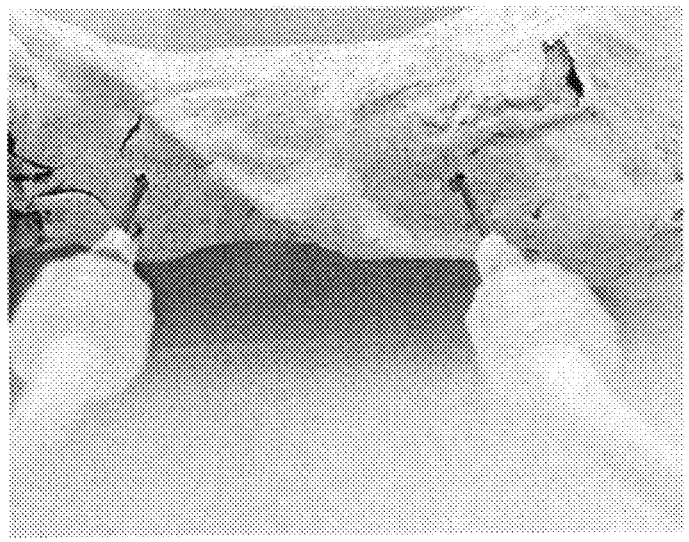
FIG. 6 is a photograph when physiological saline was introduced into the processed-bone covered with epoxy putty in Example 3.

Tubes (C-Flex Pump Tube, product number: 6424-13, manufactured by Yamato Scientific Co., Ltd.) and syringes (20-mL syringe, manufactured by TERUMO CORPORATION) were connected to two injection needles inserted into the holes of the processed-bone. Physiological saline (25 mL) was introduced into the interior of the bone from one of the syringes. FIG. 6 shows a photograph when physiological saline was introduced. The introduced liquid was collected in the other syringe. Further, the operation of introducing and collecting the liquid was repeated 3 times. Thus, physiological saline (100 mL in total) was introduced into the interior of the bone. The amount of the collected liquid was measured with a measuring cylinder. The amount of the collected liquid was 98.5 mL, and the collection rate (the amount of the collected liquid/the amount of the introduced liquid) was 98.5%.

3. Consideration

Almost all the introduced liquid was collected from the second hole. This shows that there was little leakage of the liquid from the surface of the bone. Consequently, it is thought that the leakage of the liquid from the surface of the bone can be suppressed by covering the bone with epoxy putty, whereby the cells can be collected.

Example 4

In this example, a liquid was introduced into the processed-bone prepared by the method of Example 2. Then, the number of cells contained in the collected liquid was measured. An uncovered bone was used as the control.

1. Preparation of Processed-Bone

A processed-bone made of the pig femur covered with PDMS was produced in the same manner as in Example 2. Two holes having a diameter of 1.2 mm were drilled in the femur covered with PDMS using an electric drill. Injection needles (18 G×1½", manufactured by TERUMO CORPORATION) were inserted into the holes. Two holes having a diameter of 1.2 mm were drilled in the femur extracted from a pig (LWD breed, weight: about 30 kg) as the control. Injection needles (18 G×1½", manufactured by TERUMO CORPORATION) were inserted into the holes.

2. Collection of Cells (2-1) Collection of Cells from Processed-Bone

Tubes (C-Flex Pump Tube, product number: 6424-13, manufactured by Yamato Scientific Co., Ltd.) and syringes (20-mL syringe, manufactured by TERUMO CORPORATION) were connected to two injection needles inserted into the holes of the processed-bone. Physiological saline (10 mL) was introduced into the interior of the bone from one of the syringes. Then, the introduced liquid was collected in the other syringe. The amount of the collected liquid was 10 mL, and the collection rate was 100%.

(2-2) Collection of Cells from Uncovered Femur

Tubes (C-Flex Pump Tube, product number: 6424-13, manufactured by Yamato Scientific Co., Ltd.) and syringes (20-mL syringe, manufactured by TERUMO CORPORATION) were connected to two injection needles inserted into the holes of the femur. Physiological saline (120 mL) was introduced into the interior of the bone from one of the syringes. Then, the introduced liquid was collected in the other syringe. The amount of the collected liquid was 10 mL, and the collection rate was 8.3%.

3. Measurement of Number of Cells

The liquids collected from the processed-bone and the uncovered femur were analyzed with a blood cell analyzer for animals (XT-2000iv, manufactured by SYSMEX CORPORATION), and the number of cells was measured. As a result, the number of cells measured as nucleated cells was 32,335 cells/µL in the liquid collected from the processed-bone, meanwhile the number of cells was 4,080 cells/µL in the liquid collected from the uncovered femur.

4. Consideration

In the case of the processed-bone, when 10 mL of physiological saline was introduced, 10 mL of liquid was collected. On the other hand, in the case of the uncovered bone, in order to collect 10 mL of liquid, it was necessary to introduce 120 mL (12 times as large as that of the liquid) of physiological saline. Regarding the number of cells contained in the same amount of the collected liquid, the number of the cells collected from the processed-bone was about 8 times as many as the cells collected from the uncovered bone. In other words, the collection efficiency in the case of using the processed-bone was about 96 times as much as the collection efficiency in the case of using the uncovered bone. As described above, it is found that, in the method of the present embodiment using the processed-bone, the leakage of the cell-containing liquid can be suppressed by the covering agent, whereby the cells can be efficiently collected.

What is claimed is:

1. A method of collecting cells, comprising the steps of:
preparing a processed-bone comprising a bone extracted from a living body, a covering agent and first and second holes, wherein an outer surface of the bone is covered with the covering agent attached to the outer surface of the bone, and the first and second holes penetrate through the covering agent and the outer surface of the bone into the interior of the bone;
introducing a liquid into the processed-bone from the first hole; and
collecting a cell-containing liquid from the second hole.

2. The method according to claim 1, wherein the first and second holes penetrate through the covering agent and through a periosteum or articular cartilage into the interior of the bone.

3. The method according to claim 1, wherein the liquid to be introduced into the processed-bone is a liquid culture medium, physiological saline, phosphate buffered saline, an organ preservation solution, plasma, serum or a mixture thereof.

4. The method according to claim 1, wherein the liquid to be introduced into the processed-bone comprises at least one selected from a drug, a cell, a nucleic acid, and a protein.

5. The method according to claim 1, wherein the steps of preparation, introduction, and collection are performed in a temperature range of from 4° C. to 50° C. both inclusive.

6. The method according to claim 1, wherein the covering agent is at least one selected from a resin, an adhesive, a polymer membrane, a gel, and gypsum.

7. The method according to claim 6, wherein the resin is a thermosetting resin, a thermoplastic resin or a photo-curable resin.

8. The method according to claim 7, wherein the resin is at least one selected from a silicone resin, an epoxy resin, a phenol resin, and polymethyl methacrylate.

9. The method according to claim 6, wherein the polymer membrane is at least one selected from a biopolymer membrane and a synthetic polymer membrane.

10. The method according to claim 9, wherein the biopolymer membrane contains at least one polysaccharide selected from chitosan, an alginate, and pectin.

11. The method according to claim 6, wherein the adhesive is an inorganic adhesive, a natural adhesive or a synthetic adhesive.

12. The method according to claim 1, wherein the covering agent is attached to the bone at a temperature of from 4° C. to 50° C. both inclusive.

13. A method of collecting cells, comprising the steps of:
preparing a processed-bone by covering an outer surface of a bone extracted from a living body with a covering agent; and forming first and second holes that penetrate through the covering agent and the outer surface of the bone into the interior of the bone;
introducing a liquid into the processed-bone from the first hole; and collecting a cell-containing liquid from the second hole.

14. The method according to claim 13, wherein the first and second holes penetrate through the covering agent and through a periosteum or articular cartilage into the interior of the bone.

15. The method according to claim 13, wherein the liquid to be introduced into the processed-bone is a liquid culture medium, physiological saline, phosphate buffered saline, an organ preservation solution, plasma, serum or a mixture thereof.

16. The method according to claim 13, wherein the covering agent is at least one selected from a resin, an adhesive, a polymer membrane, a gel, and gypsum.

17. A method of collecting cells, comprising the steps of:
preparing a processed-bone by forming first and second holes that penetrate through an outer surface of a bone extracted from a living body into the interior of the bone; and covering the outer surface of the bone with the covering agent;
introducing a liquid into the processed-bone from the first hole; and
collecting a cell-containing liquid from the second hole.

18. The method according to claim 17, wherein the first and second holes penetrate through the covering agent and through a periosteum or articular cartilage into the interior of the bone.

19. The method according to claim 17, wherein the liquid to be introduced into the processed-bone is a liquid culture medium, physiological saline, phosphate buffered saline, an organ preservation solution, plasma, serum or a mixture thereof.

20. The method according to claim 17, wherein the covering agent is at least one selected from a resin, an adhesive, a polymer membrane, a gel, and gypsum.

* * * * *